(12) United States Patent
Fledelius et al.

(10) Patent No.: US 6,420,125 B1
(45) Date of Patent: *Jul. 16, 2002

(54) ASSAYING FRAGMENTS OF COLLAGEN IN BODY FLUIDS

(75) Inventors: Christian Fledelius, Copenhagen; Martin Bonde, Lyngby; Per Qvist, Klampenborg, all of (DK)

(73) Assignee: Osteometer Biotech A/S, Herlev (DK)

( * ) Notice: Subject to any disclaimer, the term of this patent is extended or adjusted under 35 U.S.C. 154(b) by 0 days.

This patent is subject to a terminal disclaimer.

(21) Appl. No.: 09/641,756

(22) Filed: Aug. 21, 2000

Related U.S. Application Data (63) Continuation of application No. 08/913,806, filed as application No. PCT/EP96/01228 on Sep. 22, 1997, now Pat. No. 6,107,047.

(51) Int. Cl.[7] .................................................. G01N 33/53
(52) U.S. Cl. ........................ 435/7.1; 435/975; 530/328; 530/330; 530/388.1
(58) Field of Search .................................. 435/7.1, 7.92, 435/7.93, 7.94, 7.95, 331, 975; 436/518, 532; 530/323, 326, 327, 328, 329, 330, 389.1, 387.1, 388.1

(56) References Cited

U.S. PATENT DOCUMENTS 6,107,047 A * 8/2000 Fledelius et al. ............ 435/7.1

* cited by examiner

*Primary Examiner*—Jeffrey Stucker
(74) *Attorney, Agent, or Firm*—Pennie & Edmonds LLP (57) ABSTRACT

This invention relates, in part, to a method of measuring the rate of degradation of collagen is disclosed which comprises determining the amount in a body fluid of one or more fragments of collagen having an amino acid sequence comprising isoaspartic acid. The invention also relates to an immunological binding partner that specifically binds to an amino acid sequence of type II collagen containing an isoaspartic acid residue. The invention further relates to a synthetic peptide having an amino acid sequence of type II collagen that contains an isoaspartic acid residue.

12 Claims, 4 Drawing Sheets

ASSAYING FRAGMENTS OF COLLAGEN IN BODY FLUIDS

This is a continuation of application Ser. No. 08/913,806, filed Sep. 22, 1997, now U.S. Pat. No. 6,107,047, which was the National Stage of International Application No. PCT/EP96/01228, filed Mar. 21, 1996.

FIELD OF THE INVENTION

The present invention relates to the assaying of collagen or other protein degradation products and materials useful therefor.

BACKGROUND

Collagens and Disorders of Collagen Metabolism

Osteoporosis is the most common bone disease in humans. Primary osteoporosis, accompanied by increased susceptibility to fractures, results from a progressive reduction in skeletal bone mass. It is estimated to affect 15–20 million individuals in the USA alone. Its basis is an age-dependant imbalance in bone remodelling, i.e. in the rates of formation and resorption of bone tissue.

In the USA about 1.2 million osteoporosis-related fractures occur in the elderly each year including about 538,000 compression fractures of the spine, about 227,000 hip fractures and a substantial number of early fractured peripheral bones. Between 12 and 20% of the hip fractures are fatal because they cause severe trauma and bleeding, and half of the surviving patients require nursing home care. Total costs from osteoporosis-related injuries now amount to at least $10 billion annually in the USA (Riggs, New England Journal of Medicine, 327:620–627 (1992)).

Osteoporosis is most common in postmenopausal women who, on average, lose 15% of their bone mass in the 10 years after menopause. This disease also occurs in men as they get older and in young amenorrheic women athletes. Despite the major, and growing, social and economic consequences of osteoporosis, the availability of reliable assays for measuring bone resorption rates in patients or in healthy subjects is very limited. Other disorders entailing (and correlated with) abnormalities in collagen metabolism include Paget's disease, Marfan's syndrome, osteogenesis imperfecta, neoplastic growth in collagenous tissue, dwarfism, rheumatoid arthritis, osteoarthritis and vasculitis syndrome.

Three known classes of human collagen have been described to date. The Class I collagens, subdivided into types I, II, III, V and XI, are known to form fibrils. The amino-acid sequence of type I–III (to the extent it has been elucidated) is given in Appendix A of WO 95/08115.

Collagen type I accounts for more than 90% of the organic matrix of bone. Therefore, in principle, it is possible to estimate the rate of bone resorption by monitoring the degradation of collagen type I. Likewise, a number of other disease states involving connective tissue can be monitored by determining the degradation of collagen. Examples are collagen type II degradation associated with rheumatoid arthritis and osteoarthritis and collagen type III degradation in vasculitis syndrome.

Amino acid sequences of human type III collagen, human pro α1(II) collagen, and the entire prepro α1(III) chain of human type III collagen and corresponding cDNA clones have been investigated and determined by several groups of researchers; see Loil et al., Nucleic Acid Research 12:9383–9394 (1984): Sangiorgi et al., Nucleic Acids Research, 13:2207–2225 (1985); Baldwin et al., Biochem J., 262:521–528 (1989); and Ala-Kokko et al., Biochem. J., 260:509–516 (1989).

Type I, II, and III collagens are all formed in the organism as procollagen molecules, comprising N-terminal and C-terminal propeptide sequences, which are attached to the core collagen molecules. After removal of the propeptides, which occurs naturally in vivo during collagen synthesis, the remaining core of the collagen molecules consists largely of a triple-helical domain having terminal telopeptide sequences which are non-triple-helical. These telopeptide sequences have an important function as sites of intermolecular crosslinking of collagen fibrils extracellularly. The alphaheical region also includes crosslinkable sites.

Intermolecular cross-links provide collagen fibrils with biomechanical stability. The formation of these cross-links is initiated by modification of lysine and hydroxylysine residues to the corresponding aldehydes. Several of these residues located on adjacent chains of collagen will spontaneously form different intermolecular cross-links. The exact position of the sites for cross-linking on collagen telopeptides and from the helical region has been previously described. See, for example, Kühn, K., in Immunochemistry of the extracellular matrix, 1:1–29, CRC Press, Inc., Boca Raton, Fla. (1982), Eyre, D. R., Ann.Rev. Biochem., 53:77–48 (1984) or U.S. Pat. No. 5,140,103 and 5,455,179. Furthermore, the amino acid sequences of some potential sites for cross-linking in type I, II, and III collagen are given in Table 1 below.

The fibrous proteins, collagen and elastin, are cross-linked by a unique mechanism based on aldehyde formation from lysine or hydroxylysine side chains. Four homologous loci of cross-linking are evident in molecules of type I, II and III collagens (for review see Kühn, K., in Immunochemistry of the extracellular matrix, 1:1–29 (1982)). Two are aldehyde sites, one in each telopeptide region. The other two sites are hydroxylysine symmetrically placed at about 90 residues from each end of the molecule. When collagen molecules pack into fibrils, these latter sites in the helical region align and react with telopeptide aldehydes in adjacent molecules. There is now strong evidence that 3-hydroxypyridinium residues are the mature cross-link coming from hydroxylysine-derived aldehydes. The mature cross-linking residues of the other pathway, i.e. from aldehyde formation of lysine residues, are however, still unknown.

As illustrated by formula in EP-0394296 discussed below, the two 3-hydroxypyridinium cross-links have been found to be hydroxylysyl pyridinoline (also known simply as "pyridinoline") and lysyl pyridinoline (also known as "deoxypyridinoline"). These cross-linking compounds are naturally fluorescent. Some hydroxylysyl pyridinoline cross-link are found to be glycosylated as discussed for instance in EP-A-0424428.

However, as described in Last et al, Int. J. Biochem. Vol. 22, No. 6, pp 559–564 (1990), other crosslinks occur naturally in collagen.

Prior Art Assays for Collagen Degradation

In the past, assays have been developed for monitoring degradation of collagen in vivo by measuring various biochemical markers, some of which have been degradation products of collagen.

For example, hydroxyproline, an amino acid largely restricted to collagen, and the principal structural protein in bone and all other connective tissues, is excreted in urine. Its excretion rate is known to be increased in certain conditions, notably Paget's disease, a metabolic bone disorder in which bone turnover is greatly increased, as discussed further below.

For this reason, urinary hydroxyproline has been used extensively as an amino acid marker for collagen degradation; Singer, F. R. et al., Metabolic Bone Disease, Vol. II (eds. Avioli, L. V., and Kane, S. M.), 489–575 (1978), Academic Press, New York.

U.S. Pat. No. 3,600,132 discloses a process for the determinetion of hydroxyproline in body fluids such as serum, urine, lumbar fluid and other intercellular fluids in order to monitor deviations in collagen metabolism. The Patent states that hydroxyproline correlates with increased collagen anabolism or catabolism associated with pathological conditions such as Paget's disease, Marfan's syndrome, osteogenesis imperfecta, neoplastic growth in collagen tissues and in various forms of dwarfism.

Bone resorption associated with Paget's disease has also been monitored by measuring small peptides containing hydroxyproline, which are excreted in the urine following degradation of bone collagen; Russell et al., Metab. Bone Dis. and Rel. Res. 4 and 5, U.S. Pat. No. 2,250,262 (1981), and Singer, F. R., et al., supra.

In the case of Paget's disease, the increased urinary hydroxyproline probably comes largely from bone degradation; hydroxyproline, however, generally cannot be used as a specific index for bone degradation. Much of the hydroxyproline in urine may come from new collagen synthesis (considerable amounts of the newly made protein are degraded and excreted without ever becoming incorporated into tissue fabric), and from turnover of certain blood proteins as well as other proteins that contain hydroxyproline.

Furthermore, about 80% of the free hydroxyproline derived from protein degradation is metabolised in the liver and never appears in the urine. Kiviriko, K. I., Int. Rev. Connect. Tissue Res. 593 (1970), and Weiss, P. H. and Klein, L., J. Clin. Invest. 48:1 (1969). Hydroxyproline is a good marker for osteoporosis as it is specific for collagen in bones even if it is not specific for bone resorption, but it is troublesome to handle.

Hydroxylysine and its glycoside derivatives, both peculiar to collagenous proteins, have been considered to be more accurate than hydroxyproline as markers of collagen degradation. However, for the same reasons described above for hydroxyproline, hydroxylysine and its glycosides are probably equally non-specific markers of bone resorption; Krane, S. M. and Simon, L. S., Develop. Biochem. 22:185 (1981).

Other researchers have measured the cross-linking compound 3-hydroxypyridinium in urine as an index of collagen degradation in joint diseases. See, for background and as examples, Wu and Eyre, Biochemistry, 23:1850 (1984): Black et al., Annals of the Rheumatic Diseases, 43:969–973 (1986); and Seibel et al., The Journal of Dermatology, 16:964 (1989). In contrast to the present invention, these prior researchers have hydrolysed peptides from body fluids and then looked for the presence of free 3-hydroxypyridinium residues.

Assays for determination of the degradation of type I, II, and III collagen are disclosed in EP-0394296 and U.S. Pat. No. 4,973,666 aA U.S. Pat. No. 5,140,103. However, these Patents are restricted to collagen fragments containing the cross-linker 3-hydroxypyridinium. Furthermore, the above mentioned assays require tedious and complicated purifications from urine of collagen fragments containing hydroxypyridinium to be used for the production of antibodies and for antigens in the assays.

At present very few clinical data using the approach described in U.S. Pat. Nos. 4,973,666 and 5,140,103 are available. Particularly, no data concerning the correlation between the urinary concentration (as determined by methods described in the above mentioned patents) of 3-hydroxypyridinium containing telopeptides of type I collagen and the actual bone loss (as determined by repeated measurements by bone densiometry) have been published. The presence of 3-hydroxypyridinium containing telopeptides in urine requires the proper formation in bone tissue of this specific cross-linking structure at various times before the bone resorbing process. Very little information on these processes is available and it would be desirable to avoid this dependence of the correct formation of the cross-linking structure.

GB Patent Application No. 2205643 reports that the degradation of type III collagen in the body can be quantitatively determined by measuring the concentration of an N-terminal telopeptide from type III collagen in a body fluid. This method uses antibodies generated to N-terminal telopeptides released by bacterial collagenase degradation of type III collagen, said telopeptides being labelled and used in the assay.

Schroter-Kermani et al., Immunol. Invest. 19:475–491 (1990) describe immunological measurement systems based on CNBr fragments of collagen type I and II. Use is made of pepsin-solubilised collagen, leaving the telopeptides in the tissue (cf. the above mentioned GB Patent Application No. 2205643). There is therefore no conformity between the fragments and the antibodies raised therefrom. Further, the reference only describes measurements on extracted tissue samples.

The development of a monoclonal antibody raised against pepsin-solubilised type I collagen is described in Werkmeister et al., Eur. J. Biochem. 1987:439–443 (1990). The antibody is used for immunohistochemical staining of tissue segments and for measuring the collagen content in cell cultures. The measurements are not carried out on body fluids.

EP Patent Application No. 0505210 describes the development of antibody reagents by immunisation with purified cross-linked C-terminal telopeptides from type I collagen. The immunogen is prepared by solubilising human bone collagen with bacterial collagenase. The antibodies thus prepared are able to react with both cross-linked and non-cross-linked telopeptides, and cross-linkers other than pyridinoline.

International Patent Application No. WO 91/09114 discloses certain synthetic peptides which are used to promote cellular adhesion to a solid substrate. The use of the synthetic peptides as immunological reagents is not mentioned.

There are a number of reports indicating that collagen degradation can be measured by quantitating certain procollagen peptides. Propeptides are distinguished from telopeptides and alpha-helical region of the collagen core by their location in the procollagen molecule and the timing of their cleavage in vivo; see U.S. Pat. No. 4,504,587; U.S. Pat. No. 4,312,853; Pierard et al., Analytical Biochemistry 141:127–136 (1984); Niemela, Clin. Chem. 31/8:1301–1304 (1985); and Rohde et al., European Journal of Clinical Investigation, 9:451–459 (1979).

EP Patent Application No. 0298210 and No. 0339443 both describe immunological determination of procollagen peptide type III and fragments thereof. Further, a method based on the measurement of procollagen is disclosed in EP Patent Application No. 0465104.

The use of synthetic peptides with sequences derived from type IX collagen for the development of immunological reagents is disclosed in PCT Patent Application No. WO 90/0819 Likewise the application describes the use of the antibodies thus produced for the determination of type IX collagen fragments in body fluids.

U.S. Pat. No. 4,778,768 relates to a method of determining changes occurring in articular cartilage involving quantifying proteoglycan monomers or antigenic fragments thereof in a synovial fluid sample.

Dodge, J. Clin Invest. 83:647–661 (1981) discloses methods for analysing type II collagen degradation utilising a polyclonal antiserum that specifically reacts with unwound alpha-chains and cyanogen bromide-derived peptides of human and bovine type II collagens. The degradation products of collagen were not detected in a body fluid, but histochemically by staining of cell cultures, i.e. by "in situ" detection.

WO 94/03813 describes a competitive immunoassay for detecting collagen or collagen fragments in a sample wherein a binding partner containing a synthetic linear peptide corresponding to the non-helical C-terminal or N-terminal domain of collagen is incubated with an antibody to the linear synthetic peptide and the sample, and wherein the binding of the antibody to the binding partner is determined.

WO 95/08115 relates to assay methods in which collagen fragments in a body fluid are determined by reaction with an antibody which is reactive with a synthetic peptide. The assay may be a competition assay in which the sample and such a peptide compete for an antibody, possibly a polyclonal antibody raised against fragments of collagen obtained by collagenase degradation of collagen. Alternatively, it may be an assay in which an antibody, possibly a monoclonal antibody, is used which has been raised against such a synthetic peptide.

DETAILED DESCRIPTION

One particular peptide fragment which we have found in body fluid, particularly urine, is of the formula (SEQ ID NO:1):

Formula 1

In the above formula, K—K—K represents cross-link which may for instance be a hydroxypyridinium cross-link but may be any naturally occurring cross-link and specifically any of those discussed in the above referenced paper of Last et al.

A larger peptide fragment including the above smaller fragment is reported in EP 0394296.

We have now discovered that a proportion of the "peptide" fragments in body fluid are related to peptides of equivalent amino acid sequence, e.g. peptides of formula 1, by the isomerization of aspartic acid in the formula to isoaspartic acid. We put "peptides" in quotes here as of course the isomerization means that these species are no longer properly regarded as being peptides.

The isomerization of proteins containing aspartic acid has been reported previously to be a spontaneous reaction occurring under physiological conditions.

See for instance Brennan et al., Protein Science 1993, 2, 331–338, Galletti et al., Biochem. J. 1995, 306, 313–325, Lowenson et al., Blood Cells 1988, 14, 103–117 and Oliya et al., Pharmaceutical Research, Vol. 11, No. 5, 1994, 751.

The isomerization has the effect of transferring that Dart of the peptide chain which runs downstream of the aspartic acid residue in the carboxy terminus direction from the alpha carboxylic acid of the aspartic acid to which it is bonded via a peptide bond in the normal protein to the side chain carboxylic acid in a non-peptide amide bond, as shown below:

The non-peptide bonded aspartic acid residue is termed "isoaspartic acid".

Similar isomerization can occur in proteins containing asparagine residues (i.e. with —NH$_2$ instead of —OH in the starting protein in the above reaction scheme).

The above discovery indicates that this isomerization also occurs in bone tissue and the extent of isomerization is expected therefore to be marker for the age of the bone tissue concerned.

Furthermore, the presence amongst such bone peptide fragments of the isomerized peptides provides confirmation that the fragments indeed derive from bone degradation and not some other source such as the degradation of newly formed collagen never incorporated into bone.

Accordingly, the present invention now provides in a first aspect a method of measurement of the rate of degradation of a body protein such as collagen, e.g. from bone, comprising determining the amount of one or more isoaspartic acid containing species in a body fluid.

The isomerized peptides in question may be characteristic of type I, type II or type III collagen, but preferably are characteristic of type I collagen.

More preferably, such a method determines the amount of one or more specific isoaspartic acid containing isomerized peptides present in said body fluid.

Preferably, the method determines the amount of the isomerized peptide of formula 2 (below) present in said body fluid (SEQ ID NO:2):

Formula 2 wherein one or both of * is isoaspartic acid, or of one or more isomerized peptides incorporating an epitope present in the isomerized peptide of formula 2 which contains isoaspartic acid.

In the above formula, K—K—K is a cross-link such as a hydroxypyridinium cross-link which may be pyridinoline (which may be glycosylated or non-glycosylated) or deoxypyridinoline.

Preferably, said determination is carried out using an immunological binding partner specific for an isoaspartic acid containing species present in the sample during the procedure, preferably said isomerized peptide of formula 2 or a isomerized peptide incorporating an epitope present in the isomerized peptide of formula 2 which contains isoaspartic acid.

The immunological binding partner may be a monoclonal or polyclonal antibody. By the requirement that the immunological binding partner be specific for the isoaspartic acid containing species is meant that the immunological binding partner distinguishes between said species and the analogous aspartic acid containing species (peptide) to an extent useful in the assay.

Suitable immunological binding partners also include fragments of antibodies capable of binding the same antigenic determinant including Fab, Fab' and F(ab')$_2$ fragments.

Preferably, the immunological binding partner is an antibody raised against a linear isomerized peptide, preferably a synthetic isomerized peptide, corresponding to a sequence within collagen with isoaspartic acid substituting in said amino acid sequence for aspartic acid in said collagen protein sequence.

The assay may take many forms including ELISA, RIA, or IRMA, procedures for which are too well known to warrant description here.

In a second aspect, the invention includes the use in an assay for collagen derived isomerized peptides of a synthetic isomerized peptide having an amino acid sequence corresponding to a sequence within collagen with isoaspartic acid substituting in said amino acid sequence for aspartic acid in said collagen protein sequence. In a competition assay, the said synthetic isomerized peptide may be used to compete for an immunological binding partner with one or more isomerized peptides in the sample.

In an ELISA of this type, the synthetic peptide may be immobilised on a solid support. A sample may be incubated with a polyclonal antibody for the synthetic isomer of a peptide in contact with the solid support and after washing, a peroxidase-conjugated (revealing) antibody may be added. After further incubation, a peroxidase substrate solution is added. By competition, peptide isomer in the sample reactive with the antibody inhibits the peroxidase reaction.

Alternatively, the synthetic peptide isomer may be used to raise a monoclonal immunological binding partner. The synthetic isomerized peptide need not then be a competing agent in the assay. For instance, collagenase treated collagen may be purified and immobilised onto the solid support and an ELISA may be carried out using a monoclonal antibody.

Accordingly, in a third aspect, the invention includes an antibody, preferably a monoclonal antibody, specific for an amino acid sequence corresponding to a sequence within a protein, e.g. collagen with isoaspartic acid substituting in said amino acid sequence for aspartic acid in said protein, e.g. collagen sequence.

In a preferred embodiment of this aspect of the invention, the antibody is specific for an isomerized peptide sequence including the sequence EKAHiDGGR (SEQ ID NO:3) or containing an epitope specific for the presence of iD present in said sequence, wherein iD is isoaspartic acid.

Accordingly, this aspect of the invention includes an antibody, preferably a monoclonal antibody reactive with an epitope containing, contained in, or constituted by the peptide isomer sequence EKAHiDGGR (SEQ ID NO:3), wherein iD is isoaspartic acid.

In a fourth aspect, the invention provides an antibody, preferably a monoclonal antibody, raised against a peptide isomer having an amino acid sequence corresponding to a sequence within a protein, e.g. collagen with isoaspartic acid substituting in said amino acid sequence for aspartic acid in said collagen protein sequence.

The invention includes cell lines producing monoclonal antibodies according to the third or fourth aspects of the invention.

The invention also includes antibodies according to the third or fourth aspects of the invention coupled to a detectable marker. Suitable detectable markers include, but are not limited to, enzymes, chromophores, fluorophores, coenzymes, enzyme inhibitors, chemiluminescent materials, paramagnetic materials, spin labels, radio-isotopes, nucleic acid or nucleic acid analogue sequences.

In a fifth aspect, the invention includes the use in an assay for collagen or other protein derived isomerized peptides of an antibody specific for an amino acid sequence corresponding to a sequence within the protein, (e.g. collagen) with isoaspartic acid substituting in said amino acid sequence for aspartic acid in said protein (e.g. collagen) sequence to obtain information regarding the amount of isoaspartic acid containing peptide isomer or isomers in said body fluid.

In a sixth aspect, the invention includes a synthetic peptide isomer having an amino acid sequence corresponding to a sequence within collagen with isoaspartic acid substituting in said amino acid sequence for aspartic acid in said collagen protein sequence, preferably in at least the substantial absence of the corresponding peptide.

Preferably there is a glycine residue adjacent the aspartic acid residue in the native peptide form of the amino acid sequence, as an adjacent glycine facilitates the isomerization of aspartic acid.

Antibodies may be prepared which are respectively selective for one or more aspartic acid containing peptides and for their isoaspartic acid containing analogues. It is then possible to carry out an assay for both variants of the peptide or peptides. The relative amount of isoaspartic acid will provide an indication of the age of the protein which is being broken down protein and of the bone if the assay is for a type of collagen fragment. Accordingly, in a sixth aspect the invention provides a method of obtaining information regarding collagen resorption in a patient, comprising measuring in a body fluid the relative amounts of at least one aspartic acid containing peptide derived from collagen and a corresponding isoaspartic acid containing peptide analogue.

The invention also includes test kits useful in the methods described above. Such kits may comprise an antibody according to the third or fourth aspect of the invention, or similarly specific antibody fragment, preferably in combination with any one or more of:

a synthetic peptide analogue containing isoaspartic acid reactive with the antibody, an antibody-enzyme conjugate and/or a substrate therefor, an enzyme conjugate-substrate reaction stopping composition, or a wash solution.

The invention may be applied both to humans and to animals.

Suitable body fluids include, human or animal urine, blood, serum, plasma and synovial fluid. It is contemplated that the method may also be used e.g. on saliva and sweat. The body fluid may be used as it is, or it may be purified prior to the contacting step. This purification step may be accomplished using a number of standard procedures, including, but not limited to, cartridge adsorption and elution, molecular sieve chromatography, dialysis, ion exchange, alumina chromatography, hydroxyapatite chromatography, and combinations thereof.

The invention is described in more detail below. Reference is made to the appended drawings.

BRIEF DESCRIPTION OF THE DRAWINGS

FIG. 1 shows the HPLC separation of a synthetic peptide and a peptide analogue of the sequence EKAH*GGR (SEQ ID NO:4) differing at between isoaspartic acid (peak 2) and normal aspartic acid (peak 3) as described in Example 3a;

FIG. 2 shows the differing reactivity of the separated peptide and peptide analogue of FIG. 1 in two forms of ELISA, as described in Example 3a.

In a preferred embodiment of the method according to the invention, the assaying of type I, II, or III collagen fragments in urine or other body fluid is performed by an inhibition ELISA (enzyme linked immunosorbent assay) by metering off a sample of urine body fluid contacting the sample with a synthetic peptide analogue having a sequence derived from collagen and with an antibody, which is immunoreactive with the synthetic peptide analogue. The synthetic peptide analogue is immobilised on a solid support. The antibody may be raised against the synthetic peptide analogue or may be raised against collagen degradation products and screened for by use of such a synthetic peptide analogue.

Preparation of Synthetic Peptide Analogues

The preparation of synthetic peptides and peptide analogues may be performed according to procedures well known in the art, e.g. by solid-phase peptide synthesis techniques commonly described as "Merrifield synthesis". Also classical solution phase techniques may be used. Sequences of interest include potential sites for collagen cross-linking (see for example Kühn, K., in Immunochemistry of the extracellular matrix, 1:1–29(1982), Eyre, D. R., Ann. Rev.Biochem. 53:717–48(1984), or U.S. Pat. No. 5,140,103). Examples of such peptides sequences are given in Table 1 below. The conventional peptide synthesis method may produce a mixture of peptide (with normal peptide bonded aspartic acid) and peptide analogue with isomerization of the bonding to the aspartic acid. Generally such a mixture will be satisfactory as the peptide will be insert in the assay. However, heating such a mixture will normally produce isomerization of the peptide content to the iso-form.

Regarding the synthetic peptide analogues, it is possible to omit (or add) one or more amino acid residues from (or to) the crosslinkable site sequences without substantial loss of the ability to (a) raise antibodies recognising the isoaspartic acid analogue of the corresponding native collagen fragment or (b) inhibit the binding of such antibodies to the said analogue of the native fragment. It is possible to use longer collagen fragments and/or chimeric peptide analogues to raise the antibodies and, in principle, it is not necessary to use the same peptide analogue as the immunogen and the competitor in a competition assay.

TABLE 1

Examples of Amino Acid Sequences with Potential Sites for Crosslinking in Various Types of Collagen to be Used as a Basis for Isoaspartic Acid Containing Synthetic Peptide analogues according to the Present Invention

```
Collagen Type I
Potential sites
in telopeptide analogues:    N                                                      C
a1 (I) N-term.(Iso)Asp-Glu-Lys-Ser-Thr-Gly-Gly (SEQ ID NO:5) (a1(I)N1)
a1 (I) C-term.Glu-Lys-(Iso)-Asp-Gly-Lys-Gly-Arg (SEQ ID NO:3) (a1(I)C1)
a2 (I) N-term.Glu-Tyr-(Iso)-Asp-Gly-Lys-Gly-Val-Gly (SEQ ID NO:6) (a2(I)N1)

Collagen Type II
Potential sites
in telopeptide analogues:    N                                                      C
a1 (II) N-term.Gly-Asp-Ile-Lys-(Iso)Asp-Ile-Val(SEQ ID NO:7)
a1 (II) C-term.Glu-Lys-Gly-Pro-(Iso)Asp (SEQ ID NO:8)

Collagen Type III
Potential sites
in telopeptide analogues:    N                                                      C
a1 (III) N-term.(Iso)Asp-Val-Lys-Ser-Gly-Val (SEQ ID NO:9)
```

Preparation of Antibodies

The methods for preparation of both monoclonal and polyclonal antibodies are well known in the art. For example, see Campbell, A. M., Laboratory Techniques in Biochemistry and Molecular Biology, Vol. 12 (1986). It is possible to produce antibodies to synthetic isomerized peptides by immunisation. However, because of the relatively small molecular weight of these compounds it is preferred that the hapten be conjugated to a carrier molecule. Suitable carrier molecules include, but are not limited to, bovine serum albumin, thyroglobulin, oval-bumin, tetanus toxoid, and keyhole limpet hemocyanin. The preferred carrier is bovine serum albumin. To present the hapten in its most immunogenic form to the antibody producing cells of the immunised animal a number of alternative coupling protocols can be used. Suitable procedures include, but are not limited to, glutaraldehyde, carbodiimide, and periodate. Preferred binding agents are glutaraldehyde and carbodiimide.

The preparation of antibodies may be carried out by conventional techniques including immunisation with collagen fragments containing natural isomerization or synthetic isomerized peptides conjugated to a carrier. To improve the immunogenicity it is preferred that the immunogen be mixed with an adjuvant before injection. Examples of adjuvants include, but are not limited to, aluminium hydroxide, Freund's adjuvant, and immune-stimulating complexes (ISCOMs). ISCOMs can be made according to the method described by Morein, B. et al., Nature 308:457–460 (1984).

Either monoclonal or polyclonal antibodies to the haptencarrier molecule can be produced. For the production of monoclonal antibodies it is preferred that mice are immunised. Spleen cells from the immunised mouse are harvested, homogenised, and thereafter fused with cancer cells in the presence of polyethylene glycol to produce a cell hybrid which produces monoclonal antibodies specific for isomerized peptide fragments derived from collagen. Suitable cancer cells include, but are not limited to, myeloma, hepatoma, carcinoma, and sarcoma cells. Detailed descriptions of the production of monoclonal antibodies are provided in Goding, J. W., in Monoclonal Antibodies: Principles and Practice (1986). A preferred preliminary screening protocol comprises the use of synthetic isomerized peptides conjugated to a carrier and coated on to the solid surface of a microtitre plate.

For the preparation of polyclonal antibodies, which are reactive with isomerized peptide fragments derived from collagen, different animal species can be immunised. Suitable species include, but are not limited to, chicken, rabbit and goat. Chicken and rabbit are preferred.

Antibodies so produced may be screened for suitability for use according to the invention by testing for reactivity with an isoaspartic acid containing synthetic peptide analogue of appropriate sequence.

Antibody fragments are prepared by methods known in the art (see E. Ishikawa, Journal of Immunoassay 3:209–327 (1983))

Conduct of Immunoassays

Accordingly, by utilisation of an immunoassay with the antibodies prepared as above it is possible to assay a biological fluid sample without prior fractionation or hydrolysis. The specificity for the desired collagen fragments in the biological fluid may be supplied by the antibody in combination with the use of a synthetic isomerized peptide (against which the antibody was raised or in any event with which the antibody is immunochemically reactive) in the assay construction.

As an alternative the immunoassay may be performed using a monoclonal antibody. The basic idea of this assay design is to shift the specificity of the assay from the antigen (synthetic peptide isomer to collagen) to the antibody (from rabbit antiserum to monoclonal antibody). Using this construction the assay does not need to make further use of a synthetic peptide isomer. This version of the immunoassay is suitably performed by incubating the patient sample or a standard solution with a peroxidase-conjugated antibody solution in a microtiter plate precoated with purified collagenase-treated collagen. After washing, the wells of the plate are incubated in the dark with a substrate solution. The colour reaction is stopped by the addition of a stopping solution, and finally the absorbance is measured.

The immunoassays themselves may be conducted using any procedure selected from the variety of standard assay protocols generally known in the art. As it is generally understood, the assay is constructed so as to rely on the interaction between the specific immunological binding partner and the desired analyte for specificity and to utilise some means to detect the complex formed by the analyte and the immunological binding partner. The immunological binding partner may be complexed to a solid support and used as a capture immunological binding partner for the analyte. This protocol may be run in a direct form, wherein the formation of analyte-immunological binding partner complex is detected, e.g. by a fluorescent, radioactive or enzymatic label, or it may be run in a competitive format wherein a labelled standard competes with the analyte for the immunological binding partner. The format may also be constructed as an agglutination assay or the complex may be precipitated by addition of a suitable precipitant to the reaction mixture. The specific design of the immunoassay protocol is open to a wide variety of choice, and the number of clinical assay devices and protocols available in the art is multitudinous. For a variety of such protocols, see U.S. Pat. No. 5,001,225.

The antibodies and revealing reagents for the conduct of an immunoassay using standard detection protocols, for example radioisotope labelling, fluorescent labelling or ELISA, either in a direct or competitive format, may conveniently be supplied as kits which include the necessary components and instructions for the assay. In one embodiment of the invention such a kit includes a microtiter plate coated with a relevant synthetic isomerized peptide, standard solutions for preparation of standard curve, a body fluid (e.g. urine) control for quality testing of the analytical run, rabbit antibodies reactive with the above mentioned synthetic peptide isomer, anti-rabbit immunoglobulins conjugated to peroxidase, a substrate solution, a stopping solution, a washing buffer and an instruction manual.

Since immunoassays can be constructed using antibodies and specific synthetic isomerized peptides, the ratios of the corresponding collagen fragment sequences in an appropriate biological fluid can be determined as well as their individual levels and their total. Thus, the assay can be designed to include antibodies which will result in determination of several isoaspartic acid containing peptide analogues and optionally the native peptide sequences or determination of a single isoaspartic acid containing peptide analogue sequence, or any desired combination thereof.

In addition to the use of the herein specified isomerized peptides as indicators of bone resorption, bone metabolic balance is advantageously determined by the substantially simultaneous determination of a marker of the formation of bone in the same or other appropriate biological fluid from the same individual. "Substantially simultaneous" means the same day, preferably within 4 hours. For example such markers include osteocalcin (also known as bone GLA protein of BGP) propeptides of procollagen type I, bone alkaline phoshatase and total alkaline phosphatase. Suitable methods for the determination of these markers can be found, for example, in Delmas, P. D., et al., J. Bone Mi Res. (1986) 1:333–337.

The assay of the present invention which provides an index to determination of the metabolic status of tissues, which generate collagen-derived peptides and isomerized peptides when degradation occurs, is useful in a variety of contexts. First, when considering the degradation of type I collagen, the assays are methods to assess an abnormal condition of a subject by indicating, for example, excessive bone resorption. This may show the presence of an osteoporotic condition or the metastatic progress of a malignancy. Other conditions characterised by excessive bone resorption include Paget's disease and hyperparathyroidism. Likewise, a number of other disease states involving connective tissue may be monitored by determination of the degradation of collagen. Examples are collagen type II degradation associated with rheumatoid arthritis and osteoarthritis and collagen type III degradation in vasculitis syndrome. Since the condition of the subject can be monitored continuously, application of these assays can also be used to monitor the progress of therapy administered to treat these or other conditions. Further, the assays can be used as a measure of toxicity, since the administration of toxic substances often results in tissue degradation.

Thus the assays may be applied in any situation wherein the metabolic condition of collagen tissues can be used as an index of the condition, treatment, or effect of substances directly administered to the subject or to which the subject is exposed in the environment.

The following examples are intended to illustrate, but not to limit the invention.

EXAMPLE 1

Immunoassays for Specific Peptide Sequences in Urine

Three isomerized peptides (α1(I)C1, α1(I)N1, and α2(I) N1) (see Table 1) prepared by solid-phase techniques are used for the preparation of immunogens. For immunisation, the peptide isomers are covalently attached to bovine serum albumin using carbodiimide or glutaraldehyde reagents and methods well known in the art. Both monoclonal and polyclonal antibodies are raised against the peptide isomers. For production of monoclonal antibodies, Balb/c mice are immunised with peptide isomer-BSA conjugates, and hybridoma cell lines are prepared using standard techniques after fusion of cells from the spleen or lymph nodes with Ag8 myeloma cells. Polyclonal antibodies are raised in rabbits and chicken. Screening of both antisera and hybridoma cell media were performed by ELISA using microtiter plates coated with the appropriate peptide isomer-protein carrier conjugate prepared using carbodiimide reagents and methods well known in the art.

Assays for three of the peptide isomer sequences (α1(I) C1, α1(I)N1, and α2(I)N1) in urine are performed by an inhibition ELISA as follows:

Urine samples (10 to 25 µl) possibly containing collagen fragments or solutions containing 0.015–15 µg peptide isomer/ml as reference standards, respectively, are added to 75 µl of immunological binding partners for the peptide isomers diluted 1:5,000–1:20,000 in phosphate buffered saline containing 0.1% Tween-20 detergent (PSB-T) and including 0.1% (w/v) of BSA. Each sample is prepared in duplicate in flat-bottomed, 96-well microtiter plates previously coated with peptide isomer-protein carrier conjugate containing the appropriate peptide isomer. After 60 minutes, the plates are washed with PBS-T (3 times) and the bound antibodies are detected by standard techniques with a horseradish peroxidase labelled antibody prepared against the species of the primary antibody. Peroxidase substrate is added and the colour development is measured at 450 nm in an automated microtiter plate reader after stopping the enzyme reaction using 1 M $H_3PO_4$. Samples containing the analyte decrease the binding of primary antibody to the immobilised peptide isomer on the plate and thus have a reduced colour concentration. The amount of analyte in the sample is quantified with reference to previously established curves from standards included on each plate computed using loglin plots.

EXAMPLE 2

Assay Using a Monoclonal Antibody for Detection of Degradation Products of Type I Collagen Monoclonal antibodies were developed by immunisation of mice with isoaspartic acid containing α1(I)C1 synthetic peptide analogue conjugated to an appropriate carrier protein. Cell fusion, cloning and propagation of hybridomas were performed according to standard procedures. Screening procedures included testing of reactivity to α1(I)C1 synthetic peptide analogue immobilised on microtiter plates.

The specificity of the antibodies was tested by inhibition studies using different overlapping sequences from the C-telopeptide of type I collagen in peptide analogue form, i.e. including the isomerized linkage as aspartic acid.

An assay using one such antibody MAbA-ISO is developed. In brief, the isoaspartic acid containing synthetic peptide analogue α1(I)C1 is conjugated to bovine serum albumin using carbodiimide or glutaraldehyde, and the conjugate is used for coating of microtiter plates. Alternative material can also be used, the essential feature being exposure of the sequence EKAHiDGGR (SEQ ID NO:3) sequence.

Following coating, the wells of the microtiter plates are incubated with 15 µl of urine and 100 µl of MAbA-ISO conjugated to horseradish peroxidase.

After one hour the plates are washed and substrate (e.g. TMB) is added.

EXAMPLE 3

Correlation of Elisa for Isoaspartic Acid Peptide Analogue to Elisa Assays Based on Other Peptide Fragments and Antibodies The correlation between a polyclonal ELISA according to this invention and an MAbA7 ELISA as described in WO 95/08115 on HPLC separated peptide species, (a) synthetic and (b) isolated from urine, was evaluated. The MAbA7 ELISA is a competitive assay wherein the MAbA7 monoclonal raised against the 8AA peptide (EKAHDGGR (SEQ ID NO:10) in which D is normal aspartic acid) is used and collagen degraded collagen immobilised in a microtiter tray competes with collagen fragments in the sample for binding to the monoclonal antibody (MAbA7).

The ELISAs used in this example are carried out as follows:

(a) The Polyclonal ISO-ELISA

The polyclonal ELISA is based on an immobilised synthetic peptide analogue with an amino acid sequence of eight amino acids (8AA) specific for an isomerised part of the C-telopeptide of the α1-chain of type I collagen (Glu-Lys-AlaHis-(Iso) ASP-Gly-Gly-Arg (SEQ ID NO:3)). During incubation with an antibody reactive with this sequence, a competition takes place between the immobilised peptide iso-form analogue and the breakdown products of the α1-chain of type I collagen in the sample.

Briefly, a 25 µl sample or standard is added to each well of a formula 1 antigen-coated microplate, followed by 75 µl of antiserum raised against collagenase treated type I collagen. The plates are incubated for 1 hour at room temperature under agitation and washed five times with a washing buffer. A goat anti-rabbit immunoglobulin G horseradish peroxidase conjugate (100 µl) is added to each well. After incubation for 1 hour at room temperature, plates are washed five times as before. The enzyme substrate (100 µl/well) is added, and after 15 minutes of incubation in the dark, the reaction is stopped by adding 100 µl phosphoric acid (1 mol/L). The optical density of 450 nm is measured with a microplate reader. Duplicate measurements are performed for each sample, and the data are expressed as nanograms per mol creatinine (Cr), measured by a standard colorimetric technique. This assay is referred to herein as ISO-ELISA. The MAbA7 ELISA MAbA7 is a monoclonal antibody raised as described above in mouse against the peptide of the sequence EKAHDGGR (SEQ ID NO:10), i.e. with normal aspartic acid.

This assay version is carried out in three steps as follows:

In the first step the wells of a microtiter plate precoated with purified collagenase-treated collagen (CTC) are incubated fore 1 hour at room temperature with 15 µl standard solution or sample and 100 µl of peroxidase-conjugated monoclonal antibody solution.

After washing in the second step the wells are incubated in the dark for 15 minutes at room temperature with 100 µl substrate solution. Finally, in the third step, the colour reaction is stopped by the addition of 100 µl stopping solution. The absorbance at 450 nm is measured within 2 hours.

EXAMPLE 3(a)

This example demonstrates that antibodies specific for either synthetic EKAI-IDGGR (SEQ ID NO:10) or EKA-HiDGGR (SEQ ID NO:3) can be developed.

Figure 1:
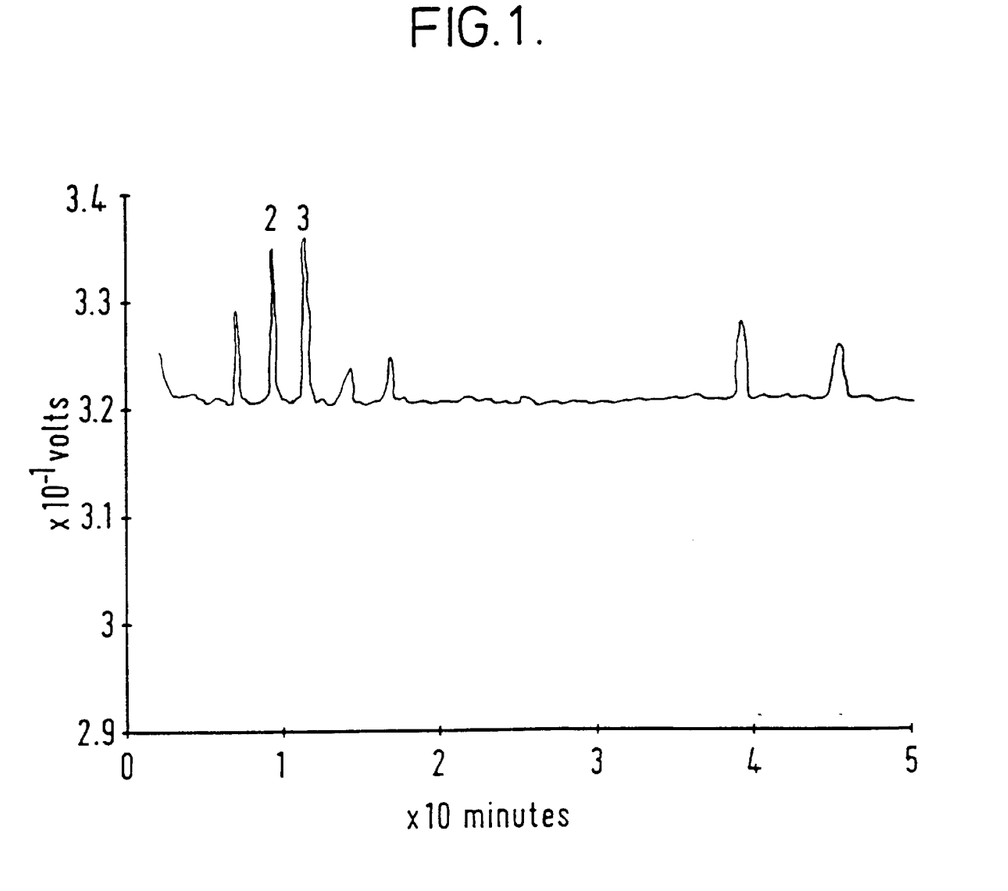

A mixture of synthetic EKAHDGGR (SEQ ID NO:10) and EKAHiDGGR (SEQ ID NO:3) was separated by HPLC (FIG. 1, peak 3 and peak 2, respectively). Sequence analysis confirmed that peak 2 contained isomerized aspartate. This was indicated by the sequencing operation being halted after the histidine residue. Peak 3 contained regular aspartate and sequencing was able to proceed normally. Fractions from the HPLC profile were collected and tested for immunoreactivity in both MAbA7 ELISA and polyclonal ISO-ELISA. It was demonstrated that the two assays detected separate peaks, i.e. peak 2 was detected by ISO-ELISA and peak 3 by MAbA7 ELISA.

Figure 2:
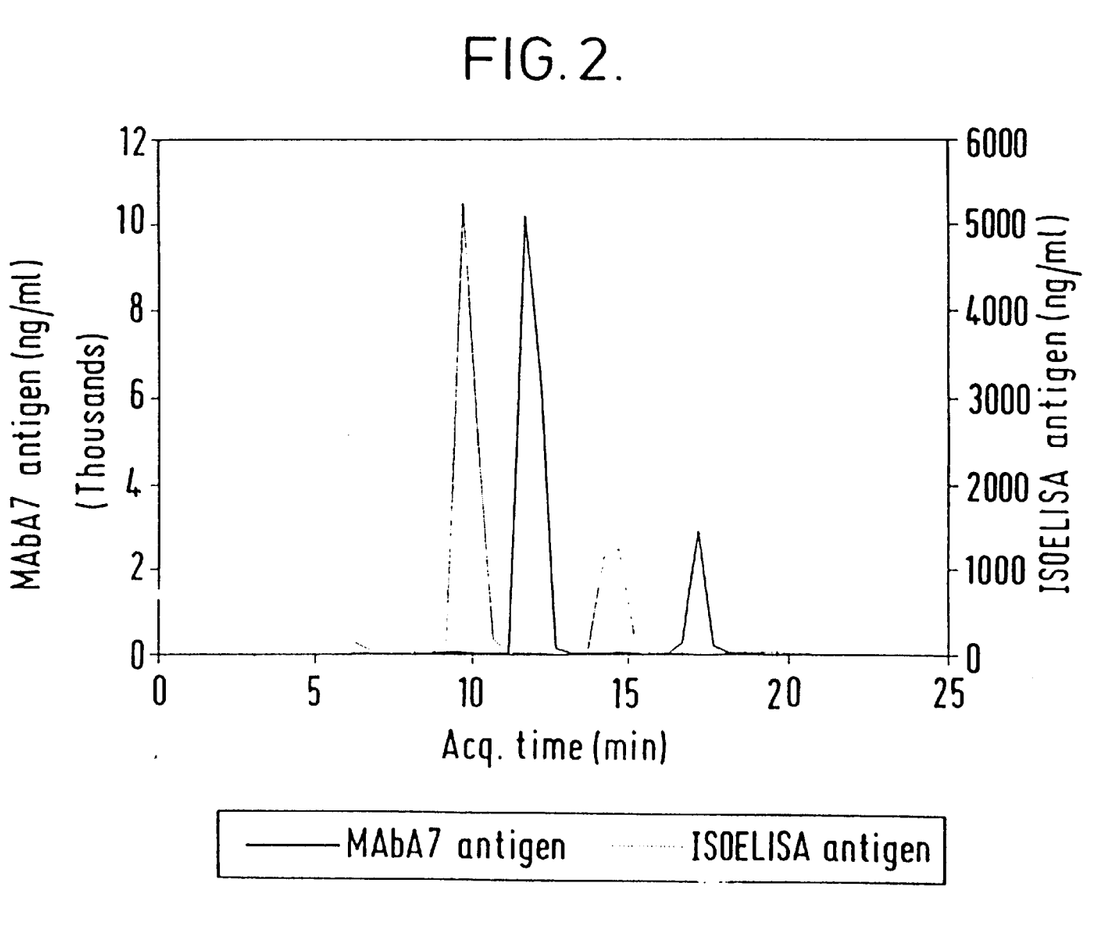

The results are shown in FIG. 2.

EXAMPLE 3(b)

This example demonstrates that ISO-ELISA-related molecules can be purified from urine, and that these molecules can be separated into di-peptide related species containing isomerized or regular aspartate.

First urine was immunopurified using MAbA7. MAbA7 was coupled to CNBr activated Sepharose™ according to the manufacturer's instructions. Urine was diluted 1:3 (v/v) in PBS buffer and the pH adjusted to 8.0 using 1 M NaOH. Eight-hundred ml diluted urine was recirculated on to a column (14 cm³) for 24 hr at 4° C. at a flow rate of 0.8 ml/min. After washing the column with 200 ml PBS buffer, pH 8.0, bound antigens were eluted using 20 ml 50% saturated $(NH_4)_2SO_4$ containing 1% TFA (v/v) and stored at −20° C. The eluted antigens were desalted using a 1 ml C18 Sep-Pak column. The Sep-Pak~column was conditioned with 20 ml 80% methanol (v/v) and equilibrated with 20 ml water containing 1% TFA (v/v) before adding the antigen. Bound antigens were washed with 20 ml of water containing 1% TFA (v/v) and eluted with 40% acetonitrile (v/v) containing 0% TFA (v/v), freeze-dried and stored at −20° C.

Molecules from selected peaks obtained by the above procedure were further separated by HPLC using trifluoroacetic acid (TFA) as ionpair. Fractions were analysed by amino acid composition, amino acid sequencing, mass spectrometry, and immunoreactivity in MAbA7 and ISO-ELISA.

Figure 3A:
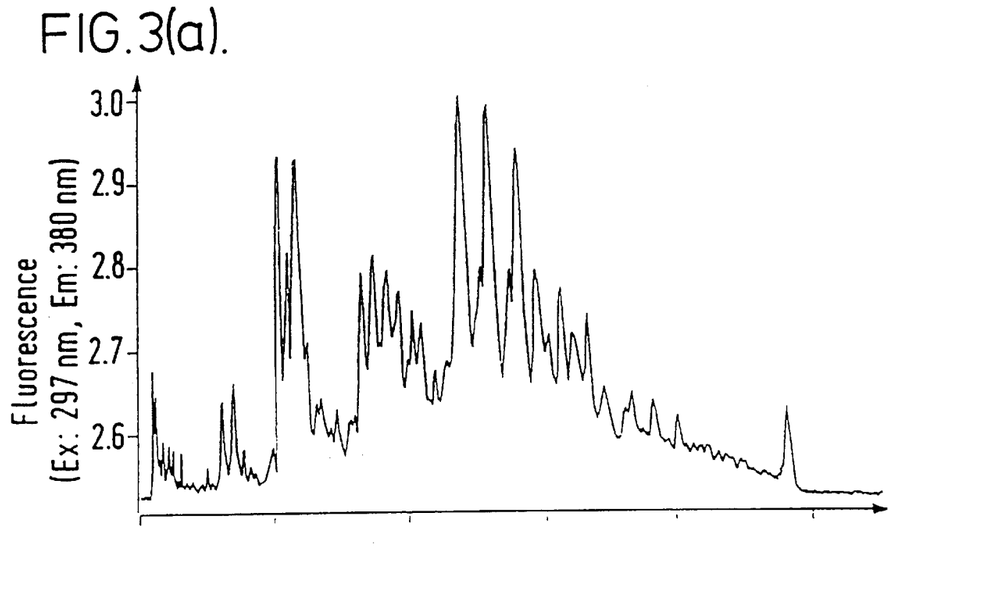
FIGS. 3(a) and 3(b) show the fluorescence (a) and absorbance (b) of crosslinked peptides and peptide analogues from urine separated by HPLC as described in Example 3 (b).
Figure 3B:
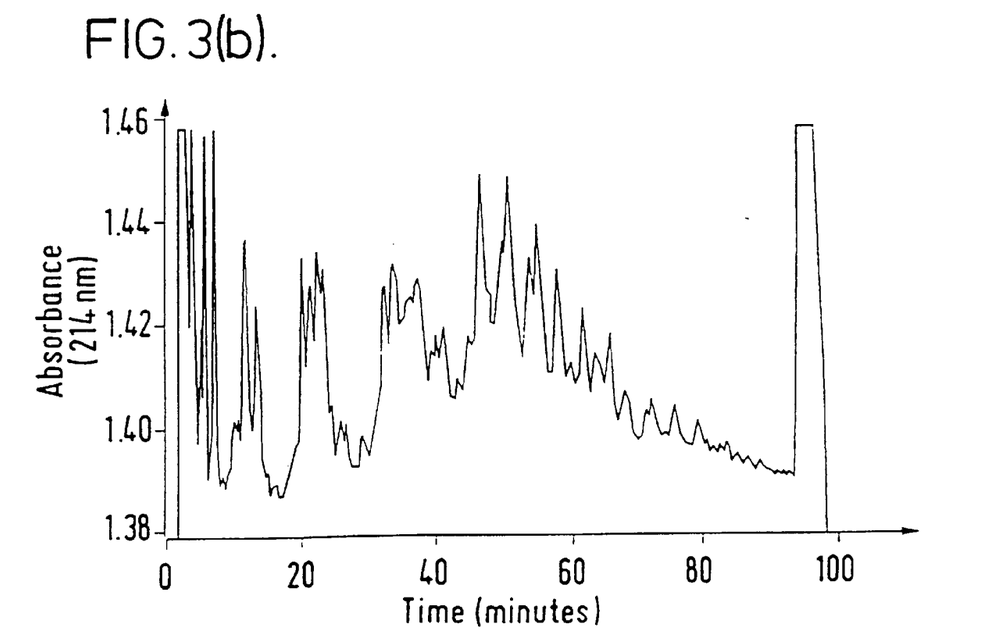

The fluorescence (3-hydroxypyridinium cross-links) and absorbance of the HFBA HPLC profile is demonstrated in FIG. 3. By further separation pure preparations were obtained and tested by mass spectrometry and immunoreactivity (Table 2) as well as amino acid sequencing (Table 2) and amino acid composition (Table 4). Data demonstrates that three separate molecules all with the molecular weight around 2036 kDaltons could be identified (Table 2). Amino acid sequencing was blocked after histidine in peak F-24-17-10, whereas the complete sequence EKAHDGGR (SEQ ID NO:10) was obtained for the two other peaks (F-26-18-09 and F-29-19-24, Table 3). Amino acid composition analysis (which does not separate isomerised and regular aspartate) confirmed the three peaks contained the same amino acids.

These data suggest that three different, cross-linked dipeptide related species were identified in urine. The molecules differed in having either isomerised or regular aspartate in the sequence EKAHDGGR (SEQ ID NO:10). Peak F-24-17-10 is suggested to contain two peptide analogues of the sequence EKAHiDGGR (SEQ ID NO:3), peak F-26-18-09 one EKAHiDGGR (SEQ ID NO:3) and one EKAHDGGR (SEQ ID NO:10), and peak F-29-19-24 two cross-linked peptides of the sequence EKAHDGGR (SEQ ID NO:1).

Additionally, a similar observation was done on molecules of molecule weight around 2039. These did not contain 3-hydroxypyridinium cross-links (as fluorescence was absent) and the nature of the cross-linker was not determined.

TABLE 2

Detection by MAbA7 and ISO-ELISA of Peptide related species separated by HPLC from Urine

| Fraction No. | Mass | Pyr | DPyr | MAbA7 ng/ml | ISO-ELISA ng/ml |
| --- | --- | --- | --- | --- | --- |
| F-18-17-14 | 2038.2 | | | 58 | 974 |
| F-20-18-18 | 2039.5 | | | 406 | 350 |
| F-22-18,19,20-16 | 2038.9 | | | 972 | 118 |
| F-24-17-10 | 2036.1 | + | | 114 | 2110 |
| F-26-18-09 | 2036.2 | + | | 2114 | 2203 |
| F-26-18-12 | 1858.9 | | + | 85 | 783 |
| F-29-19-24 | 2036.0 | + | | 3149 | 221 |
| F-30-20-12 | 1858.8 | | + | 2108 | 33 |

TABLE 3

Sequence Data for Peptide related molecules in F-24-17-10, F-26-18-09, and F-29-19-24

| Cycle | F-24-17-10 | F-26-18-09 | F-29-19-24 | Expected |
| --- | --- | --- | --- | --- |
| 1 | Glu | Glu | Glu | Glu |
| 2 | — | — | — | — |
| 3 | Ala | Ala | Ala | Ala |
| 4 | His | His | His | His |
| 5 | — | Asp | Asp | Asp |
| 6 | — | Gly | Gly | Gly |
| 7 | — | Gly | Gly | Gly |
| 8 | — | Arg | Arg | Arg |
| 9 | — | — | — | — |
| 10 | — | — | — | — |

TABLE 4

Amino Acid Composition of the Peptides F-24-17-10, F-26-18-09, and F-29-19-24 (residue/peptide)

| Amino Acid | F-24-17-10 | F-26-18-09 | F-29-19-24 | Expected |
| --- | --- | --- | --- | --- |
| Asp | 1.0 | 1.0 | 0.9 | 1 |
| Glu | 1.3 | 1.2 | 1.3 | 1 |
| Ser | 0.4 | 0.2 | 0.6 | — |
| Gly | 2.2 | 2.0 | 2.4 | 2 |
| His | 1.4 | 1.0 | 1.0 | 1 |
| Thr | 0.1 | 0.0 | 0.2 | — |
| Ala | 1.0 | 1.0 | 1.0 | 1 |
| Pro | 0.0 | 0.0 | 0.0 | — |
| Tyr | 0.0 | 0.0 | 0.0 | — |

TABLE 4-continued

Amino Acid Composition of the Peptides
F-24-17-10, F-26-18-09, and F-29-19-24 (residue/peptide)

| Amino Acid | F-24-17-10 | F-26-18-09 | F-29-19-24 | Expected |
|---|---|---|---|---|
| Val | 0.1 | 0.1 | 0.1 | — |
| Met | 0.0 | 0.0 | 0.0 | — |
| Ile | 0.1 | 0.1 | 0.1 | — |
| Leu | 0.1 | 0.1 | 0.2 | — |
| Lys | 0.3 | 0.1 | 0.3 | — |
| Arg | 0.8 | 0.9 | 0.8 | 1 |
| Total | 8.8 | 7.6 | 9.0 | 7 |

The polyclonal assay is shown to be specific for the peptide analogue containing isoaspartic acid residues and the MAbA7 assay is specific for the peptide containing normal aspartic acid residues. Di-peptide analogues containing both the isomerised as well as the non-isomerised aspartic acid will be detected by both assays.

The application of these two assays to a urine sample therefore allows a comparison to be made of the level of the normal form, giving an indication of the degree to which old established bone tissue is being broken down.

EXAMPLE 4

The clinical significance of the presence of isomerised peptide analogues in serum was investigated by subjecting serum samples from postmenopausal women taken before and after treatment with a bisphosphonate, Ibandronate (Boehringer Mannheim), to analysis in both a serum version of the ISO-ELISA polyclonal assay described above and the MAbA7 based ELISA monoclonal assay.

The assay developed for measurement of type I degradation products in serum is based on an immobilised synthetic peptide/peptide isomer mixture with the amino acid sequence EKAHDGGR (SEQ ID NO:10) present in peptide and in peptide isomer form. Rabbits were immunised with the isomerized peptide conjugated to BSA using a two step carbodiimide procedure. If the isomerized peptide is substantially more antigenic in the rabbits employed than the peptide form of the amino acid sequence one can immunise with the peptide/peptide isomer mixture conjugated to BSA. For coating of microtitre plates the peptide was conjugated to thyroglobulin using glutaraldehyde. During incubation with this antibody a competition takes place between the immobilised peptide isomer (the immobilised peptide being inactive in the assay) and the breakdown products of type I collagen in serum. As the content of the peptide in the solution increases, less antibody will bind to the immobilised peptide isomer leading to a decreasing optical density.

In brief, 50 µl Standard (synthetic 8AA-peptide isomer/peptide mixture) or unknown sample in a test tube is added 100 µl Assay Buffer (500 mM TRIS, 0.0% Tween 20, 1.0% BSA; pH=6.5). From these 150 µl, 50 µl is pipetted into the appropriate wells in the pre-coated ELISA plate. Then Antibody Solution (rabbit antiserum to EKAHiDGGR (SEQ ID NO:3) diluted 1+20.000 in Assay Buffer) is added to each well, the plate is covered with sealing tape and incubated at room temperature for 60 min on a shaking device. All the following procedures were also carried out at room temperature. After incubation the plates were washed three times with diluted Washing Buffer (25 mmol/l TRIS and 50 mmol/l NaCl pH=7.2).

Peroxidase conjugated Antibody (HRP-conjugated goat antibodies to rabbit IgG (Jackson Immunochemicals, Pa.)) diluted 1+4000 in Assay Buffer, 100 µl/well) was added and the sealed wells were incubated 60 min on a shaking device. Following another washing procedure, 100 µl of TMB Substrate Solution was added to all wells which were sealed and incubated for 15 min. The enzyme reaction was stopped after 15 min by addition of 100 µl Stopping Solution. The optical density was read in an ELISA-reader at 450 nm.

A calibration curve was constructed on a log-linear graph paper by plotting the mean absorbances of the five standards (25 ng/ml–500 ng/ml). The concentration of EKAHiDGGR (SEQ ID NO:3) equivalent in each patient specimen were determined by interpolation on the calibration curve.

Figure 4:
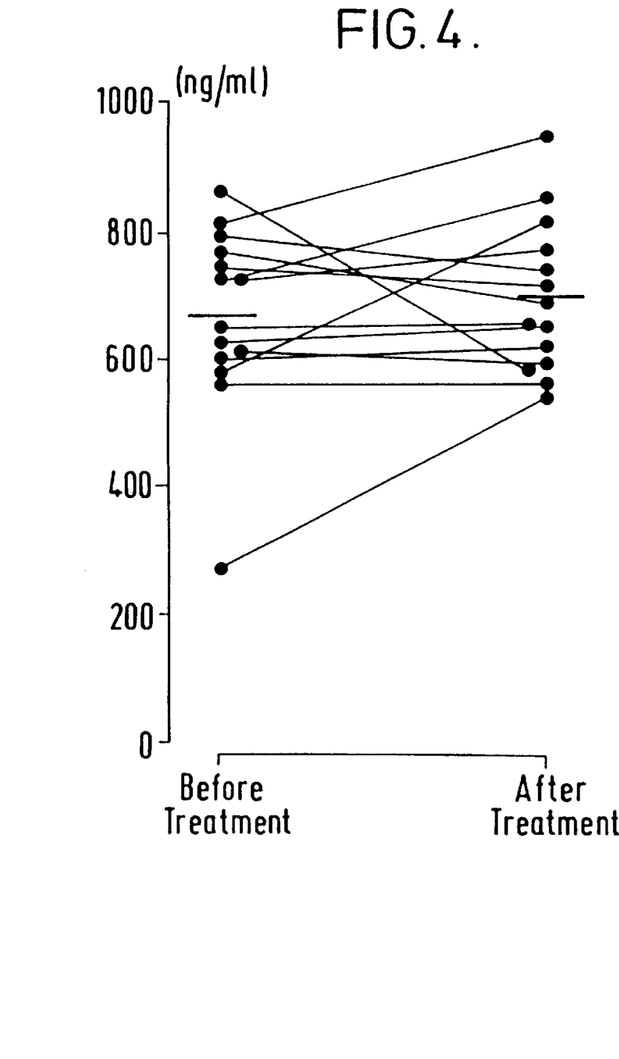
FIGS. 4 and 5 show the results of assays on serum using different antibodies to monitor the effect of bisphosphonate treatment on bone resorption.
Figure 5:
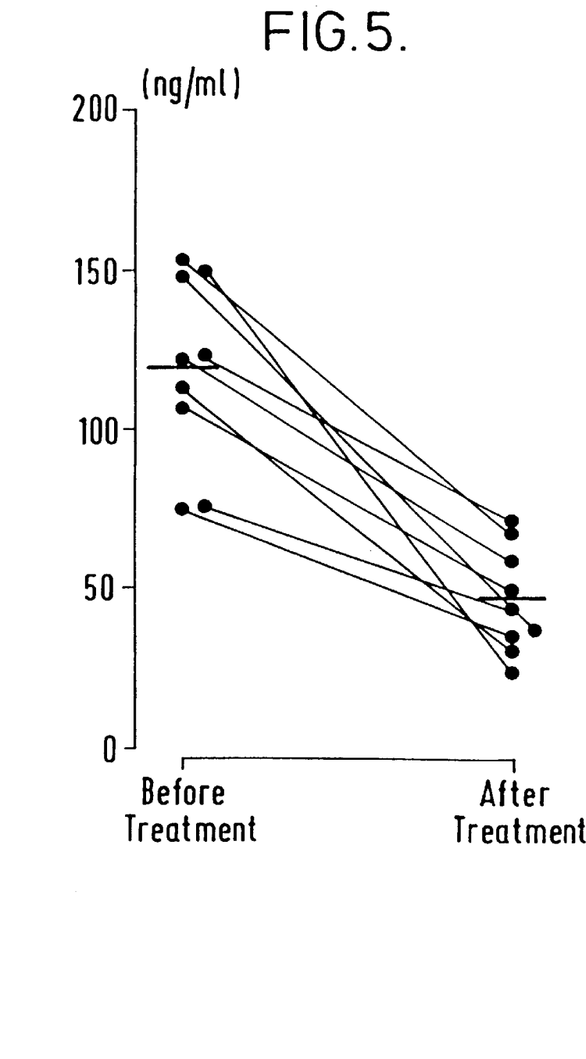

The results are shown in FIGS. 4 and 5. In FIG. 4, no significant change is seen in the serum level of molecules reactive in the monoclonal assay directed to molecules competing for antibody reactive with the peptide sequence EKAHDGGR (SEQ ID NO:10) before and after fifteen months treatment with a therapeutic expected to reduce the rate of bone resorption. In FIG. 5, one sees a drop of more than 60% following treatment for six months with 2.5 mg/day of Ibandronate in the level of molecules reactive in the polyclonal assay directed to molecules competing with the non-peptide EKAHiDGGR (SEQ ID NO:3) for antibody in the polyclonal serum, reflecting the expected result of the therapeutic treatment.

This example indicates that the sum of peptides in serum incorporating the sequence EKAHDGGR (SEQ ID NO:10), which may include cross-linked peptides of the kind described in U.S. Pat. No. 5,455,179 and similar molecules based on other cross-links or not cross-linked at all, are not indicators of the rate of bone resorption, but that the related non-peptide molecules produced by isomerisation of the bonding of the aspartic acid in the amino acid sequence are.

It is suggested that the specificity for the isomerised analogue of the octapeptide leaves the ISO-ELISA insensitive to molecules present in serum which are reactive in the MAbA7 ELISA. The level of isomerisation is believed to be related to the age of the bone, being therefore a quantifiable marker for turnover of mature bone, whilst the molecules interfering in the monoclonal assay do not relate to bone resorption and could originate from the turnover of "young" collagen molecules, e.g. from proteolytic breakdown of extracellular collagen not yet incorporated into the bone matrix, or generated during turnover of short-lived type I collagen at non-skeletal sites.

Furthermore, although it is believed that the body has mechanisms for repairing damage to proteins by isomerisation at aspartate, it may be that in bone collagen is shielded from these repair mechanisms making isomerisation an unusually good indicator of the resorption of "old" collagen in the case of bone.

Whilst the invention has been described with reference to specific examples, many variations thereof are possible within the scope of the invention. For instance the invention may be applied to the aspartic acid or asparagine containing proteins generally and not only to collagens.

What is claimed is:

1. A method of measuring the rate of degradation of collagen comprising determining the amount in a body fluid of one or more fragments of type II collagen having an amino acid sequence comprising isoaspartic acid.

2. The method of claim 1 wherein the fragment of type II collagen comprises the amino acid sequence Gly-Asp-Ile-Lys-(Iso)Asp-Ile-Val (SEQ ID NO: 7) or Glu-Lys-Gly-Pro-(Iso)Asp (SEQ ID NO: 8).

3. The method of claim 1 wherein said determination is carried out using an immunological binding partner that specifically binds to said amino acid sequence comprising isoaspartic acid.

4. The method of claim 3 wherein the immunological binding partner was raised against an amino acid sequence comprising the amino acid sequence Gly-Asp-Ile-Lys-(Iso)Asp-Ile-Val (SEQ ID NO: 7) or Glu-Lys-Gly-Pro-(Iso)Asp (SEQ ID NO: 8).

5. An immunological binding partner that specifically binds to an amino acid sequence of type II collagen containing an isoaspartic acid residue.

6. The immunological binding partner of claim 5 wherein the amino acid sequence is Gly-Asp-Ile-Lys-(Iso)Asp-Ile-Val (SEQ ID NO: 7) or Glu-Lys-Gly-Pro-(Iso)Asp (SEQ ID NO: 8), or an epitope included in one of said sequences that contains isoaspartic acid.

7. The immunological binding partner of claim 5, wherein said immunological binding partner is a monoclonal antibody or an active fragment thereof.

8. A cell line producing the monoclonal antibody of claim 7.

9. A test kit for measuring type II collagen degradation, comprising the monoclonal antibody or active fragment thereof of claim 7.

10. The immunological binding partner of claim 5, wherein said immunological binding partner is coupled to a detectable marker.

11. A synthetic peptide having an amino acid sequence of type II collagen that contains an isoaspartic acid residue.

12. The synthetic peptide of claim 11 wherein the amino acid sequence is Gly-Asp-Ile-Lys-(Iso)Asp-Ile-Val (SEQ ID NO: 7) or Glu-Lys-Gly-Pro-(Iso)Asp (SEQ ID NO: 8).

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
       (A) LENGTH: 8 amino acids
       (B) TYPE: amino acid
       (C) STRANDEDNESS: single
       (D) TOPOLOGY: unknown (ii) MOLECULE TYPE: peptide (ix) FEATURE:
       (A) NAME/KEY: Other
       (B) LOCATION: 2
       (D) OTHER INFORMATION: Pyridinoline or deoxypyridinoline
           cross-link to lysine residue at position 2 of identical
           second chain.

(xi) SEQUENCE DESCRIPTION: SEQ ID NO:1:

Glu Lys Ala His Asp Gly Gly Arg
 1               5

(2) INFORMATION FOR SEQ ID NO:2:

(i) SEQUENCE CHARACTERISTICS:
       (A) LENGTH: 8 amino acids
       (B) TYPE: amino acid
       (C) STRANDEDNESS: single
       (D) TOPOLOGY: unknown (ii) MOLECULE TYPE: peptide (ix) FEATURE:
       (A) NAME/KEY: Other
       (B) LOCATION: 2
       (D) OTHER INFORMATION: Pyridinoline or deoxypyridinoline
           cross-link to lysine residue at position 2 of identical
           second chain.
       (A) NAME/KEY: Other
       (B) LOCATION: 5
       (D) OTHER INFORMATION: Aspartic Acid or Beta-Aspartic Acid (xi) SEQUENCE DESCRIPTION: SEQ ID NO:2:

Glu Lys Ala His Xaa Gly Gly Arg
 1               5

(2) INFORMATION FOR SEQ ID NO:3:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Other
       (B) LOCATION: 5
       (D) OTHER INFORMATION: Beta-Aspartic Acid (xi) SEQUENCE DESCRIPTION: SEQ ID NO:3:

```
Glu Lys Ala His Xaa Gly Gly Arg
 1               5
```

(2) INFORMATION FOR SEQ ID NO:4:

(i) SEQUENCE CHARACTERISTICS:
        (A) LENGTH: 8 amino acids
        (B) TYPE: amino acid
        (C) STRANDEDNESS: single
        (D) TOPOLOGY: linear     (ii) MOLECULE TYPE: peptide     (ix) FEATURE:
        (A) NAME/KEY: Other
        (B) LOCATION: 5
        (D) OTHER INFORMATION: Aspartic Acid or Beta-Aspartic Acid     (xi) SEQUENCE DESCRIPTION: SEQ ID NO:4:

```
Glu Lys Ala His Xaa Gly Gly Arg
 1               5
```

(2) INFORMATION FOR SEQ ID NO:5:

(i) SEQUENCE CHARACTERISTICS:
        (A) LENGTH: 7 amino acids
        (B) TYPE: amino acid
        (C) STRANDEDNESS: single
        (D) TOPOLOGY: linear     (ii) MOLECULE TYPE: peptide     (ix) FEATURE:
        (A) NAME/KEY: Other
        (B) LOCATION: 1
        (D) OTHER INFORMATION: Beta-Aspartic Acid     (xi) SEQUENCE DESCRIPTION: SEQ ID NO:5:

```
Xaa Glu Lys Ser Thr Gly Gly
 1               5
```

(2) INFORMATION FOR SEQ ID NO:6:

(i) SEQUENCE CHARACTERISTICS:
        (A) LENGTH: 8 amino acids
        (B) TYPE: amino acid
        (C) STRANDEDNESS: single
        (D) TOPOLOGY: linear     (ii) MOLECULE TYPE: peptide     (ix) FEATURE:
        (A) NAME/KEY: Other
        (B) LOCATION: 3
        (D) OTHER INFORMATION: Beta-Aspartic Acid     (xi) SEQUENCE DESCRIPTION: SEQ ID NO:6:

```
Gln Tyr Xaa Gly Lys Gly Val Gly
 1               5
```

(2) INFORMATION FOR SEQ ID NO:7:

(i) SEQUENCE CHARACTERISTICS:
        (A) LENGTH: 7 amino acids
        (B) TYPE: amino acid
        (C) STRANDEDNESS: single
        (D) TOPOLOGY: linear     (ii) MOLECULE TYPE: peptide     (ix) FEATURE:
        (A) NAME/KEY: Other (B) LOCATION: 5
            (D) OTHER INFORMATION: Beta-Aspartic Acid (xi) SEQUENCE DESCRIPTION: SEQ ID NO:7:

Gly Asp Ile Lys Xaa Ile Val
1               5

(2) INFORMATION FOR SEQ ID NO:8:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Other
            (B) LOCATION: 5
            (D) OTHER INFORMATION: Beta-Aspartic Acid (xi) SEQUENCE DESCRIPTION: SEQ ID NO:8:

Glu Lys Gly Pro Xaa
1               5

(2) INFORMATION FOR SEQ ID NO:9:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Other
            (B) LOCATION: 1
            (D) OTHER INFORMATION: Beta-Aspartic Acid (xi) SEQUENCE DESCRIPTION: SEQ ID NO:9:

Xaa Val Lys Ser Gly Val
1               5

(2) INFORMATION FOR SEQ ID NO:10:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:10:

Glu Lys Ala His Asp Gly Gly Arg
1               5